(12) United States Patent
Both et al.

(10) Patent No.: US 7,091,012 B2
(45) Date of Patent: Aug. 15, 2006

(54) PROCESSES FOR OBTAINING STEROLS AND POLAR LIPIDS FROM VEGETABLE OIL LECITHIN FRACTIONS

(75) Inventors: Sabine Both, Duesseldorf (DE); Teresa Alexandre, Krefeld (DE); Bernhard Gutsche, Hilden (DE); Juergen Kray, Langenfeld (DE); Carsten Beverungen, Duesseldorf (DE); Rainer Eickenberg, Duesseldorf (DE)

(73) Assignee: Cognis Deutschland GmbH & Co., KG, Duesseldorf (DE)

( * ) Notice: Subject to any disclaimer, the term of this patent is extended or adjusted under 35 U.S.C. 154(b) by 0 days.

(21) Appl. No.: 10/988,743

(22) Filed: Nov. 15, 2004

(65) Prior Publication Data

US 2005/0130281 A1    Jun. 16, 2005

(30) Foreign Application Priority Data

Nov. 14, 2003 (DE) ................................. 103 53 150

(51) Int. Cl.
*C12P 7/40* (2006.01)
(52) U.S. Cl. ................ 435/136; 435/135; 554/83
(58) Field of Classification Search ............ 554/83; 435/135, 136
See application file for complete search history.

(56) References Cited

U.S. PATENT DOCUMENTS 2,415,313 A    2/1947    Thurman
2,445,931 A    7/1948    Beckel et al.
4,093,540 A *  6/1978    Sen Gupta ................ 554/80
6,140,519 A    10/2000   Hutton et al.
6,797,172 B1   9/2004    Koseoglu et al.

FOREIGN PATENT DOCUMENTS

DE           27546      3/1964
EP           0 049 914 A1   4/1982
JP           62 39594    2/1987
WO           WO 83/03620 A1   10/1983

OTHER PUBLICATIONS

Bailey's Industrial Oil & Fat Products, vol. 1, Edible Oil & Fat Products: General Applications, Chapter 10, 5th Edition, (1996), pp. 311-395.
Sisley et al., Rev. Franc. Corps Gras, 5, (1958), pp. 307-315.

* cited by examiner

*Primary Examiner*—Deborah D. Carr
(74) *Attorney, Agent, or Firm*—John F. Daniels

(57) ABSTRACT

Processes for the simultaneous production of sterols and polar lipids, in which preparations of vegetable oil lecithin fractions are subjected to ultrafiltration and, on the one hand, the sterols in the permeate and, on the other hand, the polar lipids in the retentate are enriched. The permeate and retentate can subsequently be worked up by methods known per se.

20 Claims, No Drawings

PROCESSES FOR OBTAINING STEROLS AND POLAR LIPIDS FROM VEGETABLE OIL LECITHIN FRACTIONS

BACKGROUND OF THE INVENTION

Substances accompanying vegetable oils, such as for example soybean, rapeseed, sunflower or linseed oil, include phosphatides, proteins, carbohydrates, mucins and colloidal compounds which seriously affect the keeping qualities of the oil and promote hydrolytic and oxidative lipolysis. They interfere with refining because they greatly increase the refining loss. They also have an adverse effect on other operations. For example, they impeded crystallization during fractionation and block the pores of the catalyst during hydrogenation. In the final oil, they would gradually be deposited as a sediment and would thus make it look tainted. For all these reasons, certain oils with a significant content of these substances are degummed. In the present context, degumming means the removal of the entire group of these substance, irrespective of whether or not they are actually mucins. Degumming can be carried out in various ways. For example, the phosphatides can be partly removed by hydration. In this way, they lose their lipophilic character, precipitate from the oil and can be removed. Non-hydratable phospholipids are destroyed with acids and are then removed from the oil by separation. The acid has to be just strong enough to split the phospholipids without attacking the oil. Phosphoric acid or citric acid is mainly used for this purpose. Some oils, such as linseed oil for example, can also be degummed by heat. In this process, which is also known as "breaking the oil", the starting material is heated to 240 to 280° C. The mucins precipitate and can be removed.

Nevertheless, the lecithin fractions which accumulate during degumming contain valuable raw materials which may be used for other applications in the cosmetic, pharmaceutical and nutrition fields. Thus, the content of various phospholipids in technical lecithin fractions is generally ca. 50 to 55% by weight, sterols and sterol derivatives 1 to 10% by weight, neutral lipids 30 to 40% by weight and ceramides and cerebrosides 0.1 to 0.5% by weight.

However, problems arise from the fact that the quantities of useful products, particularly free sterols and ceramides, are very different and generally small, so that elaborate purification and concentration processes are necessary, but are not economical.

In this connection, various solvent-based processes are known from the prior art for enriching phospholipids from hydratable lecithins, in which acetone is used as an extractant or precipitant. This process is known among experts as deoiling of lecithin. The crude lecithin is extracted with acetone in order to remove the ca. 30–40% neutral lipids. Both powder-form and granulated products with a residual triglyceride content of ca. 1–2% are obtained. The disadvantage is that acetone is expensive to use and the products have only limited purity. Since acetone is a highly untypical solvent in the oil-processing industry, manufacturers of lecithin products were beginning to ask themselves as early as the end of the 80's whether permits to use this solvent would continue to be granted in the future.

Processes for working up degumming residues by ultrafiltration are also known in principle. According to U.S. Pat. No. 4,093,540 (Lever Brothers) and U.S. Pat. No. 6,797,172 (The Texas A&M University System), useful materials can be enriched by subjecting vegetable oil to ultrafiltration through a membrane. In these processes, however, all the oil, not the lecithin, is passed through a membrane. EP 0049914 A1 (Unilever) relates to the purification of lecithin by ultrafiltration. The purification of lecithins by filtration through a semipermeable membrane is also the subject of Japanese patent JP 62-039594 (Rinoru). U.S. Pat. No. 6,140,519 (Archer Daniels) also relates to an ultrafiltration process by which purified phosphatides can be produced. However, none of the processes offers a coherent teaching by which the various useful materials could be economically produced in sufficient yields and purities in a way that would be easy to carry out on an industrial scale.

Processes for fractionating deoiled lecithins are also known. They may be divided into three variants.

In the solvent process, the phosphatide-containing mixtures are dissolved in hexane or acetone and 50% by vol. ethanol is added to the resulting solution. Two phases are formed: the heavier phase mainly contains phosphatidyl inositol/phosphatidyl ethanolamine while the lighter phase essentially contains phosphatidyl choline/phosphatidyl ethanolamine [cf. Bailey's Industrial Oil & Fat Products, Volume 1, Edible Oil & Fat Products; General Applications]. The disadvantage of this process lies in the poor enrichment of a phospholipid component.

Although pure fractions can be obtained by chromatographic separation processes, such as preparative HPLC for example, the production costs are so high that economic operation is not possible.

DD 27546 (Humboldt University, Berlin), WO 83/003620 (Unilever) and EP 0049914 A1 (Unilever) describe processes in which the phospholipids are separated into fractions by membranes, i.e. ultrafiltration, and addition of polar solvents. However, the active-substance content in the fractions is comparatively small; in addition, the production of sterols and sterol derivatives is not considered.

Extraction processes for the production of sterols are also known. U.S. Pat. No. 2,415,313 (Refining Unincorporated Houston) relates to a process for enriching sterols and sterol glycosides in which corresponding vegetable oils are subjected to solvent extraction. However, neither purity nor yields are discussed. According to the teaching of U.S. Pat. No. 2,445,931 (US Secretary of Agriculture), alcohols are added to the vegetable oils to precipitate a solid which is only assumed to contain sterols and lecithins. Finally, a report published in Rev. Franc. Corps Gras 5, pp. 307–315 (1958) relates to the extraction of non-hydratable phosphatides with acetone. However, at 0.3%, the quantities of sterols thus produced are very small. Accordingly, these processes also do not offer any teaching as to how various useful materials can be simultaneously and economically produced from lecithins or lecithin-containing oil mucins.

The working up of sterols from triglyceride-containing mixtures is also known. In the first process variant, the complete mixture is saponified by addition of alkali and extracted with solvent, such as EDCL and/or heptane for example. After concentration, the sterols are obtained by cooling crystallization. In the second process variant, the mixture is transesterified with methanol in a high-pressure stage. The methyl esters obtained are then distilled off until ca. 30% free sterols are present in the residue. The free sterols are then obtained from the methyl ester mixture by cooling crystallization.

Accordingly, the problem addressed by the present invention was simultaneously to recover sterols and polar lipids in high purities from technical lecithin mixtures or lecithin-containing residues from the degumming of vegetable oils with minimal outlay on equipment and under economically acceptable conditions.

SUMMARY OF THE INVENTION

This invention relates generally to oleochemical raw materials and, more particularly, to the simultaneous production of various useful materials from the refining residues of vegetable oils.

The present invention relates to a process for the simultaneous production of sterols and polar lipids, in which preparations of vegetable lecithins are subjected to ultrafiltration and, on the one hand, the sterols in the permeate and, on the other hand, the polar lipids in the retentate are enriched, followed by working up by methods known per se.

Ultrafiltration has surprisingly proved to be a suitable process for providing useful materials in high yields and purities even from lecithin fractions which, basically, have a low content of sterols and polar lipids, especially ceramides and phospholipids.

DETAILED DESCRIPTION OF THE INVENTION

Starting Materials

Suitable starting materials for the simultaneous production are the degumming products or refining residues of vegetable oils such as, for example, soybean oil, rapeseed oil, sunflower oil, linseed oil, linola oil, thistle oil, olive oil and mixtures thereof. Lecithin fractions emanating from other sources may of course be worked up in the same way.

Nonipolar Solvents

Polar lipids and nonpolar lipids differ only negligibly in their molecular weights which makes separation difficult. Accordingly, in a preferred embodiment of the present invention, nonpolar organic solvents, preferably n-hexane, are added to the lecithin solutions before the ultrafiltration. In contrast to nonpolar lipids, polar lipids form micelles in such solvents as hexane or acetone which considerably improves the separation efficiency of the process. The concentration of the lecithins in the organic solvents can be ca. 1 to 30% by weight.

Enzymes

In a particularly preferred embodiment of the invention, enzymes of the glucosidase and/or amylase type or enzymes with glucosidase and/or amylase activities are added to aqueous lecithin preparations, so that all the acetals present in the mixture are split between sterols and glucose units. This ensures that the sterol glucosides are converted into free sterols and sugar units and the sterol yield is significantly increased. Suitable enzymes are, for example, Depol® 40 L (glucosidase from Biocatalysts), Depol® 220 L (amylase, Biocatalysts), Cellubrix® (glucosidase from Novozymes) and Novozym® 188 (glucosidase from Novozymes), beta-glucosidase (Sigma) and alpha-amylase (Sigma). The concentration used may be from 0.01 to 2% by weight and is preferably from 0.05 to 0.5% by weight enzyme, based on lecithin. The enzymes are preferably added to aqueous lecithins containing 10 to 60% by weight water. The reaction usually takes place under normal pressure at 20 to 60° C. The reaction time is typically 10 to 84 h. On completion of the reaction, the water is removed from the reaction mixture, for example by gravity. The glucose units split off from the glucosides are thus separated from the lecithin. The free sterol content in the remaining lecithin is increased by a factor of 2 to 6 by this treatment. The lecithin thus treated and dried is then further separated up in an ultrafiltration.

Carrying out the Process

In a preferred embodiment of the process, aqueous suspensions of vegetable lecithins are first treated with enzymes and the aqueous phase is removed after the enzymatic reaction. As mentioned, this preliminary step is optional. The lecithins thus treated are then dried, dissolved in a nonpolar solvent, preferably hexane, and subjected to ultrafiltration followed by diafiltration. On the one hand, the free sterols and sterol esters are enriched in the permeate and, on the other hand, polar lipids, such as ceramides and phospholipids for example, are enriched in the retentate. The two product streams are then freed from the solvent. The lipids remaining in the permeate are saponified in known manner and the sterols are extracted and crystallized. The lipids remaining in the permeate may also be transesterified with methanol. In addition, the content of sterols in the residue may be further increased by selective distillation. The sterols may then be crystallized. The polar lipids may be worked up into enriched phospholipids as a phospholipid fraction or by fractionation by ultrafiltration. The ceramides present in the retentate are then obtained as enriched fractions by solvent extraction or by addition of polar solvents and subsequent ultrafiltration. The micelles are broken by addition of weakly polar solvent. The micelles of the ceramides have proved to be less resistant than those of the phospholipids. The fractions obtained are then freed from the solvents and dried. If desired, the phospholipids may then be separated up into the phosphatidyl inositol, phosphatidyl ethanolamine and phosphatidyl choline fractions.

Ultrafiltration and Diafiltration

Ultrafiltration is the term generally used among experts for separation processes using porous membranes for removing macromolecular substances with molecular weights of $1 \times 10^3$ to $10^6$ dalton or a diameter of 0.1 to 0.001 µm. In the context of the process according to the invention, the term ultrafiltration is used for membrane microfiltration in which the various useful materials are enriched separately from one another in the permeate and retentate.

Two properties are central to the economy of any membrane process, namely: the selectivity of the membrane, i.e. its ability to distinguish between the components of a mixture, and the efficiency of the membrane, i.e. the permeate flux to be obtained under certain operating conditions. The operating conditions for ultrafiltration are governed by the dimensions of the module and, in particular, by the membrane material. Filtration is typically carried out at temperatures of 20 to 50 and preferably 30 to 40° C. and under pressures of 1 to 10 and preferably 3 to 8 bar.

Important factors in the choice of the membrane material are inter alia pore size distribution, porosity, pH compatibility, chemical and mechanical stability which the expert can determine by routine optimization without having to become involved in any inventive activity. Commonly used materials for UF membranes are polysulfone (PS), polyether sulfone (PES), cellulose acetate (CA), polyamide (PA) and polyvinylidene fluoride (PVDF). Materials to be emphasized are PVDF, which is distinguished in particular by good solvent compatibility, and polyether sulfone (PES) because it allows much narrower pore size distributions than polysulfone (PS).

The ultrafiltration is carried out in modules which can differ in shape and size. In selecting the module, a compromise has to be found between high packing density for low module costs on the one hand and good module washability or a minimal tendency towards blockages on the other hand. The pillow module (flat membranes) has the following advantages: simple inexpensive production, relatively high packing density and good material transfer.

Diafiltration is a variant of ultrafiltration which is often used to achieve more complete separation. In diafiltration, the concentrate is diluted by addition of solvent and subsequent ultrafiltration until the desired removal of the permeating material is achieved. The solvent may be supplied continuously to compensate for the loss of volume by ultrafiltration or discontinuously where the concentration is diluted after ultrafiltration carried out in batches.

In the course of ultrafiltration or combined ultra- and diafiltration, all neutral lipids, including the sterol esters and the free sterols released beforehand or already present in the starting material, pass over into the permeate while the polar lipids remain in the retentate. The sterol-rich permeates are collected, freed from the hexane and worked up in known manner by two process variants. In the first variant, the complete mixture is saponified by addition of alkali and extracted with solvent such as, for example, EDCL and/or heptane. After concentration, the sterols are obtained in purities of >90% by cooling crystallization. In the second process variant, the mixture is transesterified with methanol in a high-pressure stage. The methyl esters obtained are then distilled off until ca. 30% free sterols are present in the residue. They are then obtained from the methyl ester mixture in purities of >90% by cooling crystallization.

The polar lipids present in the retentate are then obtained as enriched fractions by solvent extraction or by addition of polar solvents and subsequent ultrafiltration. The micelles are then broken by addition of—weakly—polar solvent, the quantity of solvent, based on the retentate, being from 0.1 to 50% by weight, preferably from 1 to 15% by weight and more particularly from 2 to 10% by weight. The polar solvent, for example an aliphatic $C_{1-6}$ alcohol, preferably ethanol or isopropyl alcohol, is preferably added in stages so that the phospholipids and the ceramides are released one after the other. Between 0.1 and 3% by weight of polar solvent are added in stage 1. The micelles of the ceramides have proved to be less resistant than those of the phospholipids. They reappear first in the ultrafiltration permeate. In stage 2, a total of 3 to 6% by weight of polar solvent (the quantity mentioned includes stage 1) are added. In a subsequent ultrafiltration, phosphatidyl choline is found in the permeate. Finally, in stage 3, the polar solvent is made up to 6 to 10% by weight. In a subsequent ultrafiltration, phosphatidyl ethanolamine is found in the permeate. Lastly, the phosphatidyl inositol remains in the retentate. Through the preliminary removal of the sterol glucosides, purer fractions of ceramides and phosphatidyl inositol, phosphatidyl ethanolamine and phosphatidyl choline can now be obtained than was hitherto the case with the known processes.

The fractions obtained are then freed from the solvents and dried.

The following purities are observed:

| | |
|---|---|
| ceramides: | >60% |
| phosphatidyl ethanolamine: | >80% |
| phosphatidyl choline: | >80% |
| phosphatidyl inositol: | >80% |

EXAMPLES

Example 1

Modification of lecithin mixtures with enzymes:

The free sterols in lecithin mixtures are enriched as follows:

5 g deionized water are added to quantities of 5 g soy lecithin, after which the enzymes shown in FIG. 1 are added:

FIG. 1

Enzymes with Amylase or Glucosidase Activity

| Enzyme | Organism | Manufacturer | Activity |
|---|---|---|---|
| Glucosidase-β | Almonds | Sigma | 3.7 U/mg solid |
| Depol ® 40 L (glucosidase) | *Aspergillus* sp. | Biocatalysts | 1200 U/g |
| Depol ® 220 L (α-amylase) | *Aspergillus oryzae* | Biocatalysts | 25000 U/g |
| Novozym ® 188 (glucosidase) | *Aspergillus niger* | Novozymes | 250 U/g |
| Cellubrix ® (glucosidase) | *Trichoderma longi.* *Aspergillus niger* | Novozymes | 1350 U/g |
| α-Amylase | Porcine pancreas | Sigma | 13.4 U/g |

For each batch, 100 mg per enzyme were added to the aqueous lecithin mixtures. The mixtures were stirred for 72 h on microtiter plates according to the temperature optimum of the corresponding enzyme (between 20 and 45° C.). A glucose-specific analysis of the lower water phase and the upper organic phase was carried out by thin-layer chromatography. Oricnol in sulfiric acid was used as the glucose-specific reagent. The composition shown in Table 1 was detected:

TABLE 1

| | Composition | |
|---|---|---|
| Enzyme added | Upper phase | Lower phase |
| None | 4 Different glucosides | No glucosides |
| β-Glucosidase | 2 Different glucosides | 2 Different glucosides |
| Depol ® 40 L | 3 Different glucosides | 1 Glucoside |
| Depol ® 220 L | 4 Different glucosides | No glucosides |
| Novozym ® 188 | 4 Different glucosides | No glucosides |
| Cellubrix ® | 3 Different glucosides | 1 Glucoside |
| α-Amylase | 2 Different glucosides | 2 Different glucosides |
| Mixture of α-amylase/β-glucosidase | Glucosides just discernible | 3 Different glucosides |

It can be seen that the best glucoside breakup of the sterol glucosides is achieved by an enzyme mixture of α-amylase and β-glucosidase.

Example 2

Ultrafiltration and Subsequent Diafiltration of Pretreated Lecithins

The following test was carried out in an ultrafiltration module with a membrane area of 0.2 m² (membrane type UFM 2242 (MC=2×10⁵). The maximum feed volume was 40 L, the operating temperature max. 20 to 50° C., the operating pressure 2 to 10 bar and the volumetric flow rate at 40 bar max. 1200 l/h. The raw material used was lecithin from Example 1 to which α-amylase/β-glucosidase had been added. The concentration of the feed solution was 5% by weight lecithin in n-hexane. The test was carried out on the batch principle, i.e. the concentrate was returned to the holding/working tank. The operating parameters shown in Table 2 were adjusted. Under fixed test conditions (pressure, volumetric flow rate, temperature), the concentration passed through various stages via "holding points".

TABLE 2

Operating parameters

|  | Pressure [bar] | Temperature [° C.] | Circulation [l/h] |
|---|---|---|---|
| Soy lecithin | 2 | 25 | 1200 |
|  | 3 | 25 | 1200 |
|  | 5 | 25 | 1200 |
|  | 10 | 25 | 1200 |
| Soy lecithin | 3 | 40 | 1200 |
|  | 5 | 40 | 1200 |
|  | 10 | 40 | 1200 |

The permeate was recycled in the tank until the specific permeate volumetric flow rate IVP (1/m²h)—defined as the quotient of the volume of the permeate removed (1) and the product of the permeation time (h) and the membrane area (m²)—was constant. To this end, the permeate volumetric flow rate was measured at 15-minute intervals. The permeate was then removed until the next holding point had been reached (cf. Table 3).

TABLE 3

Concentration stages

| Conc. factor | Volume retentate [l] | Volume permeate [l] |
|---|---|---|
| 1 | 33.0 | — |
| 2 | 16.0 | 17.0 |
| 3 | 10.7 | 5.3 |
| 4 | 8.0 | 2.7 |
| 5 | 6.4 | 1.6 |
| 6 | 5.3 | 1.1 |
| 7 | 4.6 | 0.8 |

Holding points are characterized by the particular permeate yield or the volumetric concentration factor—defined as the quotient of the volume (1) to be filtered and the volume of the concentrate (1). The passage from one holding point to the next is characterized by a defined removal of permeate. The diafiltration was then carried out. n-Hexane was added to the concentrate in a ratio by volume of 1:1 and removed though the membrane. The procedure was repeated three times or six times.

The ultrafiltration and diafiltration results were verified by thin-layer chromatography. It was found that more than 97% nonpolar lipids, such as fatty acids, triglycerides and sterols, had passed into the permeate. The polar lipid structures, such as phosphatidyl choline, phosphatidyl ethanolamine, phosphatidyl inositol, and ceramide structures remain in the retentate.

Example 3

Production of Sterols from the Permeate

The n-hexane was first removed in a rotary evaporator and the mixture was freed from solvent. Analysis of the mixture showed that 5 to 7% by weight of free sterols were present in the mixture. They were worked up in two ways:

Variant 1: 100 g 5-molar sodium hydroxide were added to 100 g of the dried mixture. After heating to 90° C., the whole was stirred for 3 hours and thus completely saponified. After cooling to room temperature, the mixture was extracted three times with 80 g n-heptane. The free sterols passed into the organic phase. After the extraction, 70% by weight of the n-heptane were removed in vacuo at 50° C. The sterols were then crystallized out at 10° C., filtered off and washed with fresh n-heptane. The yield amounted to 85% of the theoretical, the sterols having a purity of >95%.

Variant 2: 80 g methanol and 0.5% by weight zinc soap (based on the mixture as a whole) were added to 400 g of the dried mixture, followed by heating to 220° C. in an autoclave. After 3 hours, the reaction was terminated. After cooling to room temperature, the mixture was freed from traces of water and methanol in vacuo at 80° C. in a rotary evaporator. The mixture was then fractionated in a column. 50% by weight of the methyl ester were removed at 160° C./5 mbar. The bottom product, which contained methyl ester and sterols, was then cooled to 110° C. and the sterols were crystallized out at 10° C., filtered off and washed with fresh n-heptane. The yield amounted to 80% of the theoretical, the sterols having a purity of >90%.

Example 4

Production of Phospholipids from the Retentate

The retentate of Example 2 was first freed from n-hexane at 10 mbar/50° C. in a rotary evaporator. GC head space analysis showed that, thereafter, n-hexane was still present in the mixture in a quantity of less than 1 ppm while the percentage content of phospholipids was ca. 97% by weight.

Example 5

Fractionation of the Phospholipids from the Retentate 0.5% by weight ethanol was added to the retentate of Example 2. Ultrafiltration was then carried out as in Example 2. After removal of the solvent, permeate I contained 62% by weight substances of ceramide structure which were detected by thin-layer chromatography (TLC). Another 3.5% by weight ethanol was added to the retentate I obtained. Ultrafiltration was then carried out as in Example 2. After removal of the solvent mixture, permeate II contained 83% by weight phosphatidyl cholines which were also detected by TLC. Another 5% by weight ethanol was added to the retentate II obtained. Ultrafiltration was then carried out as in Example 2. After removal of the solvent mixture, permeate III contained 83% by weight phosphatidyl ethanolamines which were again detected by TLC. The retentate III obtained was also removed from the solvent. 86% by weight of a phosphatidyl inositol fraction—again detected by TLC—were found.

Comparative Example C1

Working Up of an Untreated Lecithin by Ultra- and Diafiltration

The following test was carried out as in Example 2. The concentration of the feed solution was 5% by weight lecithin in n-hexane. The test was carried out on the batch principle, i.e. the concentrate was returned to the holding/working tank. The operating parameters shown in Table 2, Example 2 were adjusted. The permeate was removed until the next holding point had been reached (cf. Table 3, Example 2). The diafiltration was then carried out. n-Hexane was added to the concentrate in a ratio by volume of 1:1 and removed through the membrane. The procedure was repeated three times or six times. The ultrafiltration and diafiltration results were verified by thin-layer chromatography. It was found that more than 97% nonpolar lipids, such as fatty acids, triglycerides and sterols, had passed into the permeate. The polar lipid structures, such as phosphatidyl choline, phosphatidyl ethanolamine, phosphatidyl inositol, and ceramide structures remain in the retentate along with sterol glucosides which were detected by glucose-specific TLC analysis.

Comparative Example C2

Production of Sterols from the Permeate of an Untreated Lecithin from C1

In the first step, the permeate was freed from the solvent in a rotary evaporator. Analysis of the mixture showed that it only contained 1 to 2% by weight free sterols. They are worked up in two ways:

Variant 1: 100 g 5-molar sodium hydroxide were added to 100 g of the dried mixture. After heating to 90° C., the whole was stirred for 3 hours and thus completely saponified. After cooling to room temperature, the mixture was extracted three times with 80 g n-heptane. The free sterols passed into the organic phase. After the extraction, 70% by weight of the n-heptane were removed in vacuo at 50° C. The sterols were then crystallized out at 10° C., filtered off and washed with fresh n-heptane. The yield amounted to 81% of the theoretical, the sterols having a purity of >95%. In this Example, the sterol yield was reduced by a factor of >5.

Variant 2: 80 g methanol and 0.5% by weight zinc soap (based on the mixture as a whole) were added to 400 g of the dried mixture, followed by heating to 220° C. in an autoclave. After 3 hours, the reaction was terminated. After cooling to room temperature, the mixture was freed from traces of water and methanol in vacuo at 80° C. in a rotary evaporator. The product was then fractionated in a column. 50% by weight of the methyl ester were removed at 160° C./5 mbar. The bottom product, which contained methyl ester and sterols, was then cooled to 10° C. and the sterols were crystallized out at 10° C., filtered off and washed with fresh n-heptane. The yield amounted to 75% of the theoretical, the sterols having a purity of >90%. In this Example, the sterol yield was reduced by a factor of >5.

Comparative Example C3

Fractionation of the Phospholipids from the Retentate of an Untreated Lecithin from C1

0.5% by weight ethanol was added to the retentate of Example 2. Ultrafiltration was then carried out as in Example 2. After removal of the solvent, permeate I contained 30% by weight substances of ceramide structure which were detected by TLC. Another 3.5% by weight ethanol was added to the retentate I obtained. Ultrafiltration was then carried out as in Example 2. After removal of the solvent mixture, permeate II contained 30% by weight phosphatidyl cholines which were also detected by TLC. Another 5% by weight ethanol was added to the retentate II obtained. Ultrafiltration was then carried out as in Example 2. After removal of the solvent mixture, permeate III contained 30% by weight phosphatidyl ethanolamines which were again detected by TLC. The retentate III obtained was also freed from the solvent. 40% by weight of a phosphatidyl inositol fraction—again detected by TLC—were found.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process comprising:
   (a) providing a vegetable oil lecithin fraction comprising sterols and polar lipids; and
   (b) subjecting the vegetable oil lecithin fraction to ultrafiltration to provide a permeate enriched in the sterols and a retentate enriched in the polar lipids; wherein the vegetable oil lecithin fraction is treated, prior to ultrafiltration, with an enzyme having amylase or glucosidase activity.

2. The process according to claim 1, wherein the polar lipids comprise phospholipids and ceramides.

3. The process according to claim 1, wherein the vegetable oil lecithin fraction comprises a degumming residue of a vegetable oil.

4. The process according to claim 3, wherein the vegetable oil is selected from the group consisting of soybean oil, rapeseed oil, sunflower oil, linseed oil, linola oil, thistle oil, olive oil and mixtures thereof.

5. The process according to claim 1, wherein the enzyme is selected from the group consisting of beta-glucosidases, alpha-amylases and mixtures thereof.

6. The process according to claim 1, wherein the enzyme comprises a mixture of a beta-glucosidase and an alpha-amylase.

7. The process according to claim 4, wherein the vegetable oil lecithin fraction is treated, prior to ultrafiltration, with an enzyme having amylase or glucosidase activity.

8. The process according to claim 7, wherein the enzyme is selected from the group consisting of beta-glucosidases, alpha-amylases and mixtures thereof.

9. The process according to claim 7, wherein the enzyme comprises a mixture of a beta-glucosidase and an alpha-amylase.

10. The process according to claim 1, wherein the vegetable oil lecithin fraction is provided in a nonpolar organic solvent.

11. The process according to claim 10, wherein the nonpolar organic solvent comprises n-hexane.

12. The process according to claim 10, wherein the vegetable oil lecithin fraction is present in an amount of from 1 to 10% by weight in the nonpolar organic solvent.

13. The process according to claim 4, wherein the vegetable oil lecithin fraction is provided in a nonpolar organic solvent.

14. The process according to claim 13, wherein the nonpolar organic solvent comprises n-hexane.

15. The process according to claim 13, wherein the vegetable oil lecithin fraction is present in an amount of from 1 to 10% by weight in the nonpolar organic solvent.

16. The process according to claim 1, wherein the vegetable oil lecithin fraction is provided in a nonpolar organic solvent.

17. The process according to claim 16, wherein the nonpolar organic solvent comprises n-hexane.

18. The process according to claim 16, wherein the vegetable oil lecithin fraction is present in an amount of from 1 to 10% by weight in the nonpolar organic solvent.

19. A process comprising:
(a) providing solution of a degumming residue of a vegetable oil comprising sterols and polar lipids in a nonpolar organic solvent, wherein the vegetable oil is selected from the group consisting of soybean oil, rapeseed oil, sunflower oil, linseed oil, linola oil, thistle oil, olive oil and mixtures thereof, and wherein the residue is present in an amount of from 1 to 10% by weight in the nonpolar organic solvent; and
(b) subjecting the solution to ultrafiltration to provide a permeate enriched in the sterols and a retentate enriched in the polar lipids; wherein the solution is treated, prior to ultrafiltration, with an enzyme having amylase or glucosidase activity.

20. The process of claim 1 wherein the sterols in the permeate are isolated at a purity of<90%.

* * * * *